(12) United States Patent
Burnett et al.

(10) Patent No.: US 10,175,209 B2
(45) Date of Patent: Jan. 8, 2019

(54) LIQUID FLOW RATE MEASUREMENT DEVICE

(71) Applicant: Waters Technologies Corporation, Milford, MA (US)

(72) Inventors: Joshua A. Burnett, Taunton, MA (US); James Usowicz, Webster, MA (US); Marc Lemelin, Douglas, MA (US); Lucas O. Tiziani, Seekonk, MA (US); Aaron Lebeau, Taunton, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 347 days.

(21) Appl. No.: 14/929,785

(22) Filed: Nov. 2, 2015

(65) Prior Publication Data

US 2016/0131617 A1    May 12, 2016

Related U.S. Application Data

(60) Provisional application No. 62/076,133, filed on Nov. 6, 2014.

(51) Int. Cl.
*G01N 30/32* (2006.01)
*G01N 30/80* (2006.01)
(Continued)

(52) U.S. Cl.
CPC ............ *G01N 30/32* (2013.01); *G01N 30/80* (2013.01); *G01N 30/78* (2013.01);
(Continued)

(58) Field of Classification Search
CPC ........ G01N 30/32; G01N 30/80; G01N 30/78; G01N 2030/328; G01N 2030/027; G01N 2030/324
See application file for complete search history.

(56) References Cited

U.S. PATENT DOCUMENTS

| | | | | | |
|---|---|---|---|---|---|
| 5,004,538 | A | * | 4/1991 | Apfel | G01N 30/32 |
| | | | | | 210/101 |
| 5,520,817 | A | * | 5/1996 | Anahara | G01N 30/82 |
| | | | | | 210/198.2 |

(Continued)

FOREIGN PATENT DOCUMENTS

| | | |
|---|---|---|
| JP | H02150768 A | 6/1990 |
| JP | 2007064759 | 3/2007 |

(Continued)

OTHER PUBLICATIONS

Combined Search and Examination Report in counterpart UK Patent Application No. 1519473.1, dated Jul. 22, 2016; 10 pages.
(Continued)

*Primary Examiner* — Hezron E Williams
*Assistant Examiner* — Xin Zhong
(74) *Attorney, Agent, or Firm* — Schmeiser, Olsen & Watts LLP

(57) ABSTRACT

Apparatus and method measure the flow rate of fluid for use in calibrating fraction collection in a chromatography system. An injector inserts a detectable substance into a flow of fluid. A first detector, disposed in a path of the flow of liquid with the substance, produces a signal in response to detecting the substance in the flow of fluid. A second detector, disposed downstream from the first detector in the path of the flow of fluid with the substance, produces a signal in response to detecting the substance in the flow of fluid. A computing system receives each signal produced by the first and second detectors upon detecting the substance in the flow of fluid, and computes a volumetric flow rate of the flow of fluid based on a time interval between the signals and a volume of the path between the first and second detectors.

16 Claims, 4 Drawing Sheets

(51) Int. Cl.
*G01N 30/02* (2006.01)
*G01N 30/78* (2006.01)

(52) U.S. Cl.
CPC . *G01N 2030/027* (2013.01); *G01N 2030/324* (2013.01); *G01N 2030/328* (2013.01)

(56) References Cited

U.S. PATENT DOCUMENTS

| | | |
|---|---|---|
| 6,106,710 A | 8/2000 | Fischer et al. |
| 6,406,633 B1 | 6/2002 | Fischer et al. |
| 6,627,075 B1 | 9/2003 | Weissgerber et al. |
| 6,767,467 B2 | 7/2004 | Fischer et al. |
| 2006/0027490 A1 | 2/2006 | DeMarco |
| 2006/0075806 A1* | 4/2006 | Gilby .................... G01N 30/82 73/61.57 |

FOREIGN PATENT DOCUMENTS

| | | |
|---|---|---|
| JP | 2014102164 A | 6/2014 |
| WO | 2006/000840 | 1/2006 |

OTHER PUBLICATIONS

"Agilent 1200 Series Purification Systems", Aug. 1, 2009, Agilent Technologies; 12 pages.
Examination Report in counterpart UK Patent Application No. 1519473.1, dated Mar. 12, 2018; 3 pages.

* cited by examiner

LIQUID FLOW RATE MEASUREMENT DEVICE

RELATED APPLICATIONS

This application claims the benefit of the earlier filing date of U.S. Provisional Patent Application Ser. No. 62/076,133, filed Nov. 6, 2014 and titled "Liquid Flow Rate Measurement Device," the entirety of which is incorporated herein by reference.

FIELD OF THE INVENTION

The invention relates generally to chromatography systems. More specifically, the invention relates to systems and methods for measuring liquid flow rate in a chromatography system.

BACKGROUND

In a fraction collection system, a user often wants to collect a compound that has eluted at a particular time. To collect this compound properly, the data system controlling the fraction collector must have an accurate estimate of the fluidic flow rate at the fraction collector inlet. Accordingly, the data system needs to know the amount of time taken by the fluid to reach the fraction collector from the detector (where the compound of interest has been detected). This time, known as the "delay time," depends on the volume of the tubing connecting the detector outlet to the fraction collector inlet, in addition to the volumetric flow rate of the fluid itself. Although the tubing volume may be known, if the volumetric flow rate of the fluid is not well known, the result may be an improperly estimated delay time. An inaccurate delay time can detrimentally affect the ability of the user to recover the compound of interest completely.

Most devices for measuring fluidic flow rate require some knowledge of at least one property (specific gravity, viscosity, specific heat, etc.) of the fluid, which hinders their usability in a general setting where these fluid properties are not always known. For example, many commercially available velocimeters require calibration for the fluid being measured. Laminar flow meters, on the other hand, require knowledge of the viscosity of the fluid, whereas thermal flow meters require knowledge of the specific heat of the fluid. If a user changes the type of fluid being measured, the instrument requires recalibration Moreover, in a simple chromatographic system without flow splitting, the fluid follows a single fluidic flow path through the system; the fluid flows from the pump, through the injector, column, and detector, to reach the fraction collector. In this instance, the fluid flow rate is typically estimated to be equal to the flow rate supplied by the pump (which is typically a constant volumetric flow rate, not constant pressure). However, when the pump meters the fluid, this typically occurs at a high pressure, whereas when the fluid reaches the fraction collector, it is near atmospheric pressure. Because of the pressure drop, the fluid expands, and the volumetric flow rate at the fraction collector is higher than at the pump.

Similarly, the temperature of the fluid metered out by the pump may be different when the fluid exits the pump from its temperature upon reaching the fraction collector. In this case, the fluid may expand or contract due to the temperature difference, affecting the overall volumetric flow rate at the fraction collector. Likewise, if the pump is mixing multiple fluids together, the solvent mixture may undergo volume contraction, which can also affect the net volumetric flow rate of the fluid as it reaches the fraction collector.

Instead of a single flow path, a chromatographic system can have multiple paths because of the use of multiple detectors and flow splitting. In such a chromatographic system, the fluid flow rate as the fluid reaches the fraction collector is generally not the same as the flow rate set by the pump.

SUMMARY

All examples and features mentioned below can be combined in any technically possible way.

In one aspect, a flow rate measurement apparatus, for use in calibrating fraction collection in a chromatography system, comprises an injector inserting a detectable substance into a flow of fluid. A first detector is disposed in a path of the flow of fluid containing the detectable substance. The first detector produces a signal in response to detecting the substance in the flow of fluid. A second detector is disposed downstream from the first detector in the path of the flow of fluid containing the detectable substance. The second detector produces a signal in response to detecting the substance in the flow of fluid. A data system receives each signal produced by the first and second detectors upon detecting the substance in the flow of fluid. The data system computes a volumetric flow rate of the flow of fluid based on a time interval between the signals and a volume of the path between the first and second detectors.

Embodiments of the flow rate measurement apparatus may include one of the following features, or any combination thereof. The inserted substance may be a gas bubble, and each of the first and second detectors may be a bubble detector. The path may lead to waste downstream of the second detector. The first detector may comprise a sample-analysis detector.

The flow rate measurement apparatus may further comprise a switch apparatus that diverts the flow of fluid away from fraction collection towards at least one of the first and second detectors. The switch apparatus may be disposed downstream of the first detector to divert the flow of fluid away from fraction collection towards the second detector, or disposed upstream of the first detector to divert the flow of fluid away from fraction collection towards the first and second detectors. The substance may be inserted into the flow of fluid in response to the switch apparatus diverting the flow of fluid away from fraction collection. The switch apparatus may comprise a fraction collector including a valve assembly having a plurality of ports, a dispensing needle in fluidic communication with a first port of the plurality of ports of the valve assembly, a syringe in fluidic communication with a second port of the plurality of ports of the valve assembly, and a controller in communication with the valve assembly and syringe to draw an gas bubble through the dispensing needle into the syringe, to flush the syringe in order to push the gas bubble into a waste line in fluidic communication with a third port of the plurality of ports of the valve assembly, and to switch the gas bubble into the path of the flow of fluid.

The flow rate measurement apparatus may further comprise a sample-analysis detector disposed in the path of flowing fluid upstream of the first detector.

In another aspect, a method for measuring a flow rate of a fluid passing through a chromatography system comprises inserting a detectable substance into a flow of fluid, producing a signal, by a first bubble detector disposed in a path of the flow of fluid containing the detectable substance, in response to detecting the substance in the flow of fluid, producing a signal, by a second bubble detector disposed downstream from the first detector in the path of the flow of fluid with the detectable substance, in response to detecting the substance in the flow of fluid, and computing a volumetric flow rate of the flow of fluid based on a time interval between the signals and a volume of the path between the first and second detectors.

Embodiments of the method may include one of the following features, or any combination thereof. The inserted substance may be a gas bubble, and each of the first and second detectors may be a bubble detector. The path may lead to waste downstream of the second detector. The first detector may comprise a sample-analysis detector.

The method may further comprise switching the flow of fluid away from fraction collection in order to divert the flow of fluid towards at least one of the first and second detectors. The switching of the flow of fluid away from fraction collection in order to divert the flow of fluid towards at least one of the first and second detectors may occur downstream or upstream of the first detector. The detectable substance may be inserted into the flow of fluid occurs in response to switching the flow of fluid away from fraction collection in order to divert the flow of fluid towards at least one of the first and second detectors.

Inserting the detectable substance into the flow of fluid may comprise drawing a gas bubble through a dispensing needle into a syringe, flushing the syringe in order to push the gas bubble into a waste line, and switching a valve to place the gas bubble into the path of the flow of fluid.

In still another aspect, a chromatography system comprises a first bubble detector, a second bubble detector in coupled to the first bubble detector by tubing, and a fraction collector coupled to the first bubble detector by a first line. The fraction collector receives a flow of fluid from a sample-analysis detector through a second line. The fraction collector is operated to insert a gas bubble into the first line upstream of the first bubble detector and to direct the flow of fluid from the second line to the first line having the gas bubble inserted therein.

Embodiments of the chromatography system may include one of the following features, or any combination thereof. The chromatography system may further comprise a data system in communication with the first and second bubble detectors to receive a signal produced by each detector upon detecting the gas bubble in the flow of fluid. The data system may compute a volumetric flow rate of the flow of fluid based on a time interval between the signals and a volume of the tubing between the first and second bubble detectors.

The fraction collector may comprise a valve assembly having a plurality of ports, a dispensing needle in fluidic communication with a first port of the plurality of ports of the valve assembly, a syringe in fluidic communication with a second port of the plurality of ports of the valve assembly, and a controller operating the valve assembly and syringe to draw the gas bubble through the dispensing needle into the syringe, to flush the syringe in order to push the gas bubble into the first line upstream of the first bubble detector, and to switch the gas bubble into the flow of fluid arriving through the second line.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Flow-rate measurement apparatus and methods described herein can accurately measure the volumetric flow rates of a fluid in a chromatography system in the 0.1 to 5.0 ml/min range, which reflect a typical fluid flow rate at or near a fraction collector. Advantageously, these measurements have little dependence on the properties of the measured fluid. Combining such flow-rate measurement apparatus with a computer-driven chromatographic system enables a mapping of the effects of changing solvent composition throughout a gradient on the flow rate of the fluid. This mapping can enhance the recovery of samples in a fraction collection system throughout a chromatographic run.

In brief overview, a detectable substance, for example, a gas bubble, is introduced into a fluid stream flowing through a chromatography system. A variety of mechanisms can serve to introduce the substance into the fluid stream. The flow of fluid pushes the detectable substance along a fluidic path towards fraction collection. Detectors monitor the flow at two points in the fluidic path to detect the passage of the detectable substance past each point. The time interval for the substance to pass both detectors, combined with the known volume of the fluidic path between the two detectors, provides sufficient information to calculate the average volume velocity (i.e., volumetric flow rate) of the fluid at or near the fraction collector. Because of the known tubing volume between a detector outlet and the fraction collector inlet, this calculated volumetric flow rate enables accurate estimation of the delay time through the tubing. An accurate delay time estimate facilitates complete recovery of a compound of interest by the fraction collector.

Figure 1:
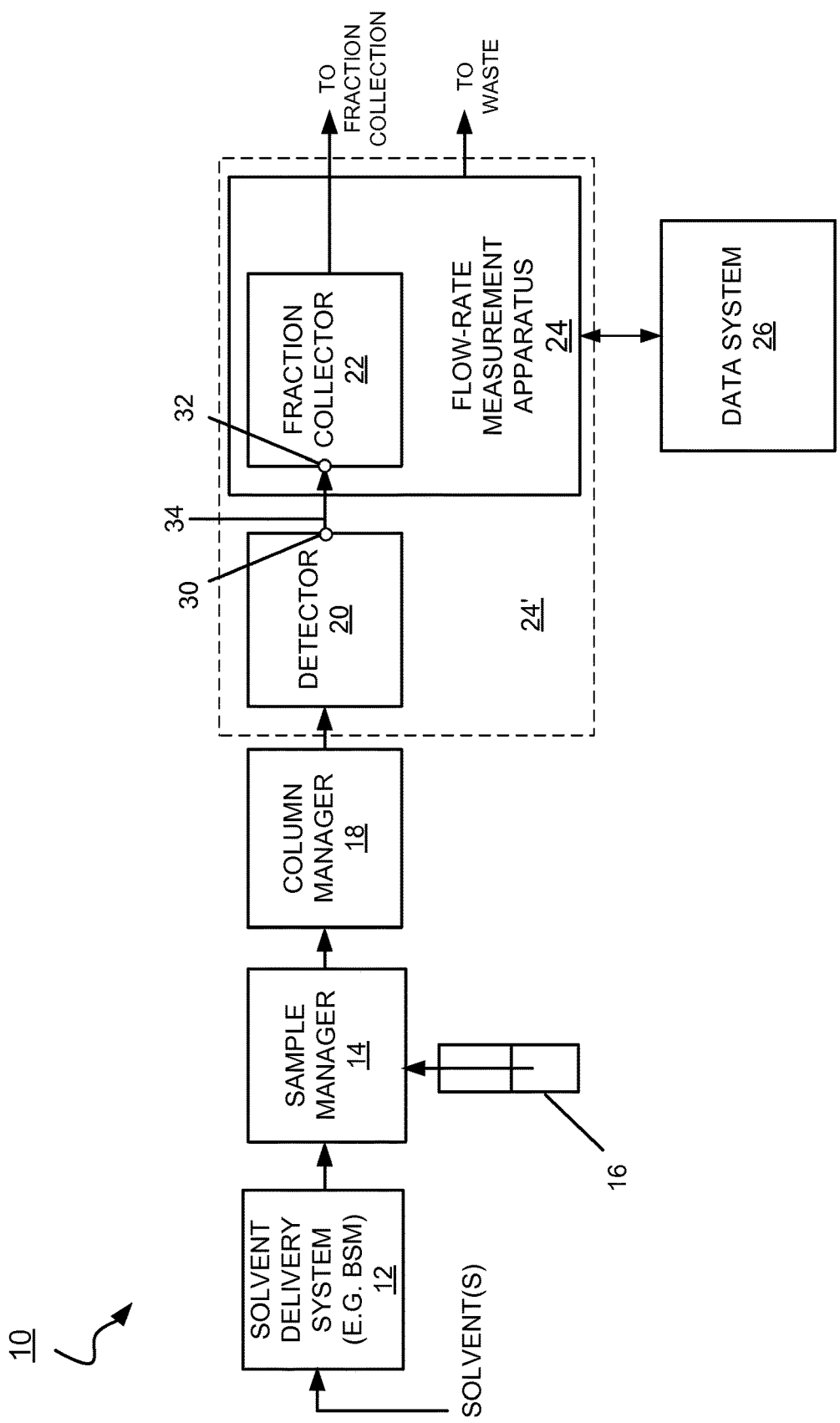
FIG. 1 is a block diagram of an embodiment of a chromatography system including a flow-rate measurement apparatus.

FIG. 1 shows an embodiment of a liquid chromatography system 10 for separating a sample into its constituents. The liquid chromatography system 10 includes a solvent delivery system 12 in fluidic communication with a sample manager 14. Generally, the solvent delivery system 12 includes pumps (not shown) in fluidic communication with solvent reservoirs from which the pumps draw solvents. The solvent delivery system 12 delivers a mixture of solvents to the sample manager 14. The sample manager 14 is in fluidic communication with a sample source 16 from which the sample manager acquires and introduces a sample to the solvent mixture arriving from the solvent delivery system 12.

In fluidic communication with the sample manager 14 is a column manager 18 for receiving therefrom the solvent composition containing the sample. The column manager 18 generally provides a controlled temperature environment for one or more chromatography separation columns used in separating sample-solvent compositions. Each separation column is adapted to separate the various components (or analytes) of the sample from each other as the mobile passes through, and to elute the analytes (still carried by the mobile phase) from the column at different times. Embodiments of the separation column include a variety of sizes (e.g., preparative, semi-preparative, analytical, or capillary-scale packed-bed columns or open tubular columns) and a variety of preparations (e.g., in conventional metallic, fused silica, or polymeric tubes, or in metallic, ceramic, silica, glass, or polymeric microfluidic platforms or substrates of various IDs).

From the column manager 18, the constituents of the separated sample pass to a detector 20 or other equipment, for example, a Flame Ionization Detector (FID), for analyzing the separation. The outlet 30 of the detector 20 is in communication with an inlet 32 of a fraction collector 22 for recovering compounds of interest resulting from the separation. The tubing 34 between the detector outlet 30 and fraction collector inlet 32 has a known volume.

As described herein, in general, a flow-rate measurement apparatus 24 introduces a detectable substance into the fluid flow and detects the substance at two spatially separate locations on a fluidic path. The flow-rate measurement apparatus 24 is in communication with a data system 26 having a processor programmed to calculate a volumetric flow rate based on the time interval between the two detections, as described below. Example embodiments of the data system 26 include, but are not limited to, fixed devices, such as desktop computers and server computers, and mobile devices, such as smart phones, smart tablets, and laptop computers.

The flow-rate measurement apparatus 24 can be an entirely separate unit, or can include components of the detector 20, the fraction collector 22, or both. In one embodiment, as shown in FIG. 1, the flow-rate measurement apparatus 24 includes the components of fraction collector 22, which receives the fluid flow from the detector 20. In another embodiment, the flow-rate measurement apparatus 24 also includes components of the detector 20 as represented generally by the box 24' with phantom outlines.

The flow-rate measurement apparatus 24 can be used for calibration purposes, that is, for calibrating the volumetric flow rate of a fluid during a test run of the chromatographic system 10, so that fraction collection can be timely performed during live (i.e., actual) runs. Such calibration runs mimic an actual run (i.e., with same flow profile), with the column(s) installed in the system 10, but normally without injecting a sample into the fluid stream. In addition, calibration runs can occur periodically, between actual runs, to update dynamically the volumetric flow rate value used for timing the fraction collection, each calibration run typically requiring less than one minute to perform, and thus imposing brief interruptions of the actual runs. Accordingly, such periodic calibration runs serve to measure flow rates (and, thus, delay times) under changing conditions, as typically occur during actual gradient runs. The data system 26 can store the progression of varying delay times in a calibration table, for use during an actual gradient run.

Figure 2:
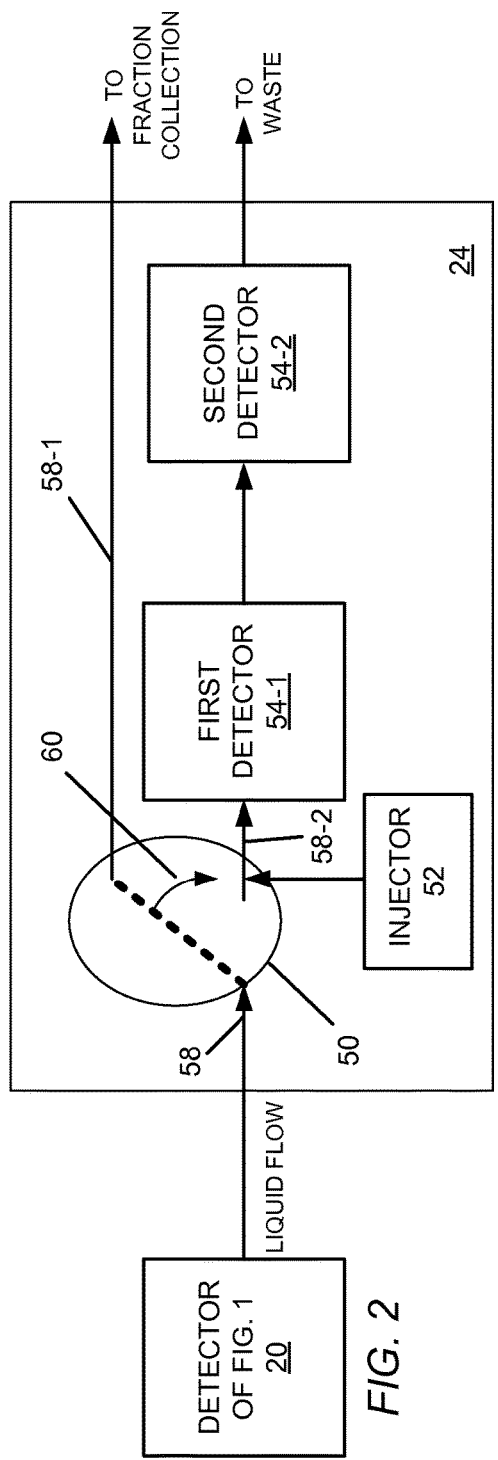
FIG. 2 is a block diagram representation of one embodiment of a flow-rate measurement apparatus.

FIG. 2 shows an abstraction of an embodiment of the flow-rate measurement apparatus 24. The flow-rate measurement apparatus 24 includes a switch apparatus 50, an injector 52, a first detector 54-1, and a second detector 54-2. The switch apparatus 50 is fluidically coupled in a flow path 58 of fluid passing through the detector 20, pumped by the solvent delivery system 12 (FIG. 1) through the liquid chromatography system 10 (FIG. 1). Based on a configuration of the switch apparatus 50, the fluid flow follows either a first flow path 58-1 towards fraction collection or a second flow path 58-2 towards waste. The first detector 54-1 and second detector 54-2 are in the flow path 58-2.

In FIG. 2, the switch apparatus 50 is in a first position, directing the flow of fluid onto the flow path 58-1. Arrow 60 signifies a second position, wherein the switch apparatus 50 diverts the fluid flow to the flow path 58-2. In general, the switch apparatus 50 is any manually or automatically controllable mechanism for controlling the direction of the flow of fluid, for example, one or more valves. The injector 52 introduces a substance (e.g., an air bubble) into the flow path 58-2 detectable by both detectors 54-1, 54-2. The substance may be referred to generally as the detectable substance. As described below, the injector 52 may cooperate with the switch apparatus 50 to introduce the detectable substance into the fluid flow. An example embodiment of the injector 52 is an automated syringe.

Figure 3:
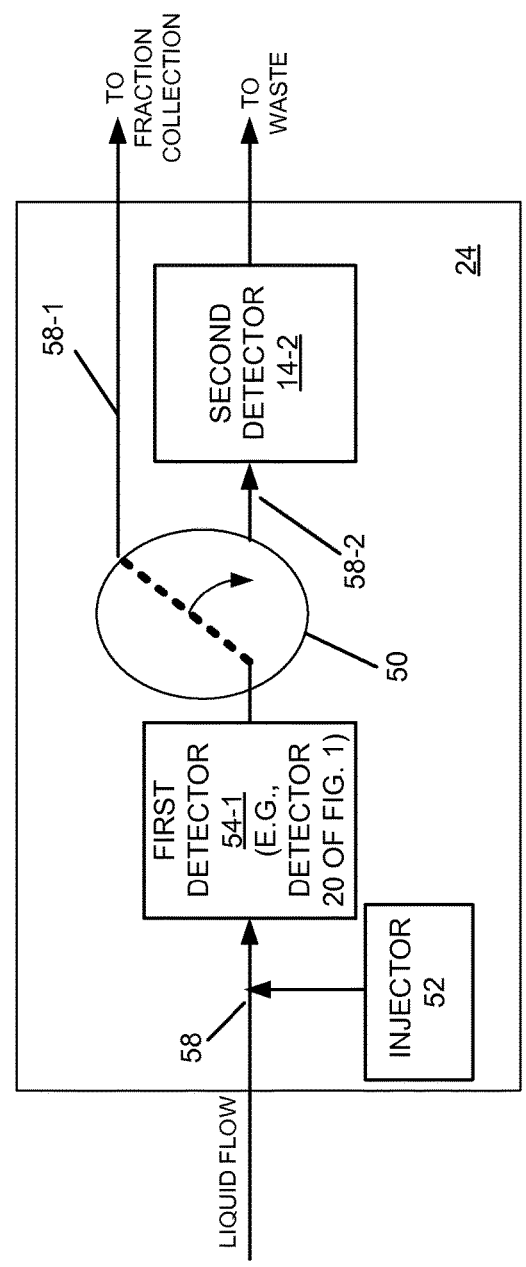
FIG. 3 is a block diagram representation of another embodiment of a flow-rate measurement apparatus.

FIG. 3 shows an abstraction of another embodiment of the flow-rate measurement apparatus 24, including the switch apparatus 50, injector 52, and first and second detectors 54-1, 54-2. Similar to the embodiment of FIG. 2, the switch apparatus 50 controls the direction of fluid flow, whether along the flow path 58-1 towards fraction collection or flow path 58-2 towards waste, the injector 52 injects a detectable substance into the fluid flow, and the detectors 54-1, 54-2 are both capable of detecting the particular type of substance introduced to the fluid stream.

Different from the embodiment of FIG. 2, the switch apparatus 50 in FIG. 3 is disposed in the flow path 58 between the first and second detectors 54-1, 54-2. This embodiment illustrates an example of a flow-rate measurement apparatus 24 that employs the detector 20 (FIG. 1) of the chromatography system 10 as the first detector 54-1. The injector 52 injects the detectable substance into the fluid flow at a point upstream of the detector 20, for example, between the column manager 18 (FIG. 1) and the detector 20, or, as another example, at the sample manager 14.

Figure 4:
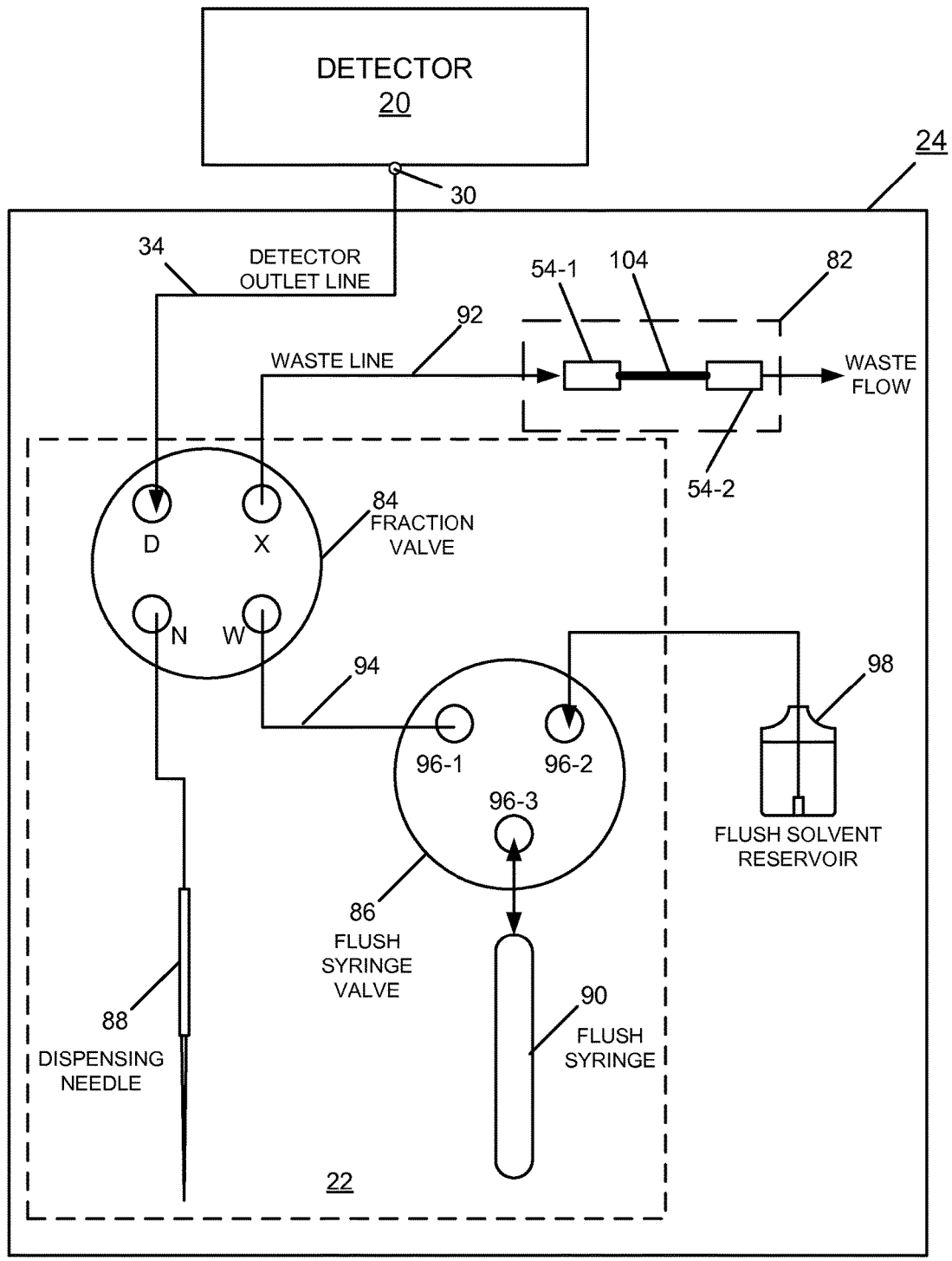
FIG. 4 is an example of the embodiment of the flow-rate measurement apparatus of FIG. 2.

FIG. 4 shows an example of the embodiment of flow-rate measurement apparatus 24 described in connection with FIG. 2. In this example, the detector 20 is in fluidic communication with the fraction collector 22 through a detector outlet line (i.e., tubing) 34. The detector outlet line 34 corresponds to the flow path 58 of FIG. 2. The functions performed by the fraction collector 22 correspond to the functions of the switch apparatus 50 and injector 52 described in connection of FIG. 2. A detector unit 82 includes the first and second detectors 54-1, 54-2 described in connection of FIG. 2.

The fraction collector 22 includes a fraction valve 84, a flush syringe valve 86, a dispensing needle 88, and a flush syringe 90. The fraction valve 84 includes four ports, labeled (clockwise) D, X, W, and N. The D port is in fluidic communication with the detector outlet line 34 that connects the fraction collector 22 to the outlet 30 of the detector 20; the X port is coupled by tubing to the detector unit 82 over a waste line (i.e., conduit) 92; the W port is coupled, by tubing, to the flush syringe valve 86 over an inter-valve connecting line 94; and the N port is coupled by tubing to the dispensing needle 88. The dispensing needle 88 and the waste line 92 are examples of the flow paths 58-1, 58-2, respectively, described in connection with FIG. 2.

The fraction valve 84 has a collect position and a waste position. In the collect position, the D port is fluidically connected to the N port such that the fluid flow coming from the detector 20 over the detector outlet line 34 passes to the dispensing needle 88. In the waste position, the D port is fluidically connected to the X port, such that the fluid flow coming from the detector 20 over the detector outlet line 34 passes through the waste line 92 to the detector unit 82. In effect, the fraction valve 84 corresponds to the switch apparatus 50 of FIG. 2.

The flush syringe valve 86 includes three ports 96-1, 96-2, and 96-3. The port 96-1 is in fluidic communication with the W port of the fraction valve 84; the port 96-2 is in fluidic communication with a flush solvent reservoir 98; and the port 96-3 is in fluidic communication with a flush syringe 90.

The detector unit 82 includes the first detector 54-1 fluidically coupled to the second detector 54-2 by a tube 104. In this example, both detectors 54-1, 54-2 are bubble detectors. Embodiments of bubble detectors include, but are not limited to, refractive index detectors and UV detectors. The first bubble detector 54-1 is in fluidic communication with the X port of the fraction valve 84 through the waste line 92. The tubing from the X port of the fraction valve 84 through the waste line 92 and the tubing 104 between the bubble detectors 54-1, 54-2, are small bore. The size of the inserted bubble fills the entire diameter of the tube. Accordingly, the progress of the bubble along the tubing is influenced by the flow rate of the fluid only and not by the orientation of the tubing. In one embodiment, the tubing has a 0.010-inch inner diameter (ID) and an inserted bubble is approximately about 20 μL in size at near-atmospheric pressure. In general, the inserted bubble is large enough so as not to become absorbed into the fluid being measured (e.g., methanol, in particular, tends to readily absorb air).

Each bubble detector 54-1, 54-2 produces a trigger signal upon detecting the gas bubble passing therethrough. Not shown is the data system 26 (FIG. 1) in electrical communication with the detector unit 82 to receive the trigger signals from the bubble detectors 54-1, 54-2 and to compute a volumetric flow rate based on the time interval between these trigger signals and on the known volume of the tubing 104 between the detectors.

The embodiment described is just an example. Other embodiment can use a different configuration of valves; for example, instead of a single four-port fraction valve 84, a series of two or three-port valves can achieve the same functionality of directing the flow output from the detector either to the waste line 92 or to the dispensing needle 88. In addition, this embodiment provides a needle rinse mechanism. Other embodiments can forego a needle rinse mechanism and use a simpler valve configuration (e.g., a three-way fraction valve) to achieve the desired flow direction.

Figure 5:
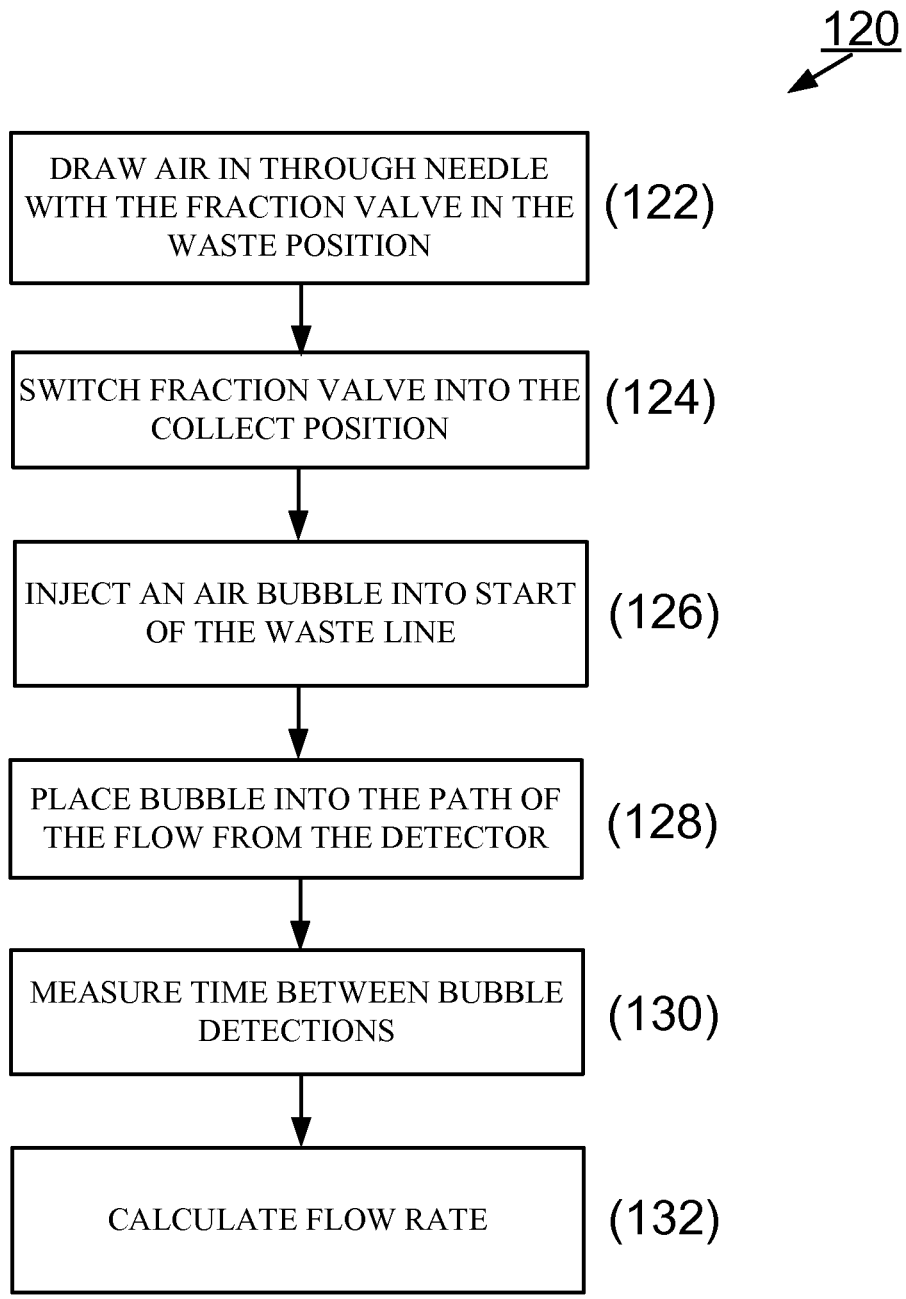
FIG. 5 is a flow diagram of an embodiment of a process for measuring the volumetric flow rate of a fluid passing through the chromatography system.

FIG. 5 shows an embodiment of a process 120 for measuring the flow rate of fluid passing through a chromatography system as part of a calibration routine before a live chromatographic run or between live runs. In the description of the process 120, reference is made to various elements of FIG. 1 and FIG. 4.

Initially, the fraction valve 84 is in the waste position, wherein the D port is connected to the X port and the N port is connected to the W port. In addition, the flush syringe valve 86 initially connects the ports 96-1, 96-3 to each other. This configuration of the valves 84, 86 produces a continuous fluidic path between the dispensing needle 88 and the flush syringe 90. In addition, fluid flow from the detector 20 passes to the waste line 92. Using the flush syringe 90, air is drawn (step 122) in through the dispensing needle 88, through the fluidic pathway between the N port and W port of the fraction valve 84, from the W port of the fraction valve 84 through the inter-valve connecting line 94 to the flush syringe valve 86, finishing with some air in the flush syringe 90 itself.

With the dispensing needle 88 positioned to drain to waste, the fraction valve 84 is switched (at step 124) to the collect position, which connects the D port to the N port and the W port to the X port. Fluid flow from the detector 20 now flows through the dispensing needle 88 into a receptacle arranged to catch the flow. Automatically controlled operation of the flush syringe 90 pushes (step 126) an air bubble to the start of the waste line 92, but without reaching the first bubble detector 54-1; the air bubble passes from the flush syringe 90 through the connected ports 96-1, 96-3 of the flush syringe valve 86, from the port 96-1 of the flush syringe valve 86 through the inter-valve connecting line 94 to the W port of the fraction valve 84, then through the connected X and W ports of the fraction valve 84 to reach the waste line 92. In the absence of fluid flow, the bubble does not move along the waste line 92 of its own accord, even if the tubing is vertically disposed.

The fraction valve 84 is then moved (step 128) back to the waste position, connecting the D port to the X port and the N port to the W port, and thereby placing the air bubble disposed at the start of the waste line 92 into the path of the fluid flow from the detector 20. Fluid flowing from the detector 20 pushes the bubble past both bubble detectors 54-1, 54-2. The data system 26 monitors (step 130) the pair of bubble detectors 54-1, 54-2 to measure the time between triggers. A processor of the data system 26 calculates (step 132) the volumetric flow rate, which is equal to volume of the tubing 104 between bubble detectors 54-1, 54-2 divided by the length of the timing interval between the triggers. From the calculated volumetric flow rate and the known volume of the tubing 34, the processor can calculate a delay time from the outlet 30 of the detector 20 to the inlet 32 of the fraction collector 22.

The process 120 is automated; a processor (or controller) controls the timing of the operation of the flush syringe 90, when to draw and push air, the amount of air to draw and push, and when to switch the fraction valve 84 in order to introduce the air bubble to the fluid stream. The processor can be part of the fraction collector 22 or of the data system 26 that calculates the volumetric flow rate.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects. All such forms may be generally referred to herein as a "system." Furthermore, aspects of the present invention may take the form of a computer program product embodied in one or more computer readable storage medium(s) having computer readable program code embodied thereon.

A computer readable storage medium may be any tangible, non-transitory medium that can contain, or store a program for use by or in connection with an instruction execution system, apparatus, or device. A computer readable storage medium may be, for example, but not limited to, an electronic, magnetic, optical, electromagnetic, infrared, or semiconductor system, apparatus, or device, or any suitable combination of the foregoing. More specific examples of the computer readable storage medium include, but are not limited to, the following: a portable computer diskette, a hard disk, a random access memory (RAM), a read-only memory (ROM), an erasable programmable read-only memory (EEPROM, EPROM, Flash memory), an optical fiber, a portable compact disc read-only memory (CD-ROM), an optical storage device, a magnetic storage device, or any suitable combination of the foregoing. Program code embodied on a computer readable storage medium may be transmitted using any appropriate medium, including but not limited to wireless, wire-line, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages.

Aspects of the present invention are described herein with reference to flowchart illustrations and block diagrams of methods, apparatus (systems), and computer program products in accordance with embodiments of the invention. Each block of the flowchart illustrations and block diagrams, and combinations of blocks in the flowchart illustrations and block diagrams can be implemented by computer program instructions.

Computer program instructions may be provided to a processor of a general purpose computer, special purpose computer, or other programmable data processing apparatus to produce a machine, such that the instructions, which execute via the processor of the computer or other programmable data processing apparatus, create means for implementing the functions, acts, or operations specified in the flowchart and block diagram block. Computer program instructions may also be stored in a computer readable storage medium that can direct a computer, other programmable data processing apparatus, or other devices to function in a particular manner, such that the instructions stored in the computer readable medium produce an article of manufacture including instructions which implement the function, act, or operation specified in the flowchart and block diagram block.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions, acts, or operations specified in the flowchart or diagram block.

The flowchart and block diagrams in the FIGS. illustrate the architecture, functionality, and operation of possible implementations of systems, methods, and computer program products according to various embodiments described herein. In this regard, each block in the flowchart or block diagrams may represent a module, segment, or portion of program code, which comprises one or more executable instructions for implementing the specified logical function(s). The functions noted in the blocks may occur out of the order noted in the FIGs. For example, two blocks shown in succession may be executed substantially concurrently, or the blocks may sometimes be executed in the reverse order, depending upon the functionality involved. In addition, each block of the block diagrams or flowchart illustration, and combinations of blocks in the block diagrams or flowchart illustration, can be implemented by special purpose hardware-based systems that perform the specified functions or acts, or combinations of special purpose hardware and computer instructions.

While the invention has been shown and described with reference to specific preferred embodiments, it should be understood by those skilled in the art that various changes in form and detail may be made therein without departing from the spirit and scope of the invention as defined by the following claims.

What is claimed is:

1. A flow rate measurement apparatus for use in calibrating fraction collection in a chromatography system, the flow rate measurement apparatus comprising:
    an injector configured to insert a detectable substance into a flow of fluid;
    a first detector disposed in a path of the flow of fluid containing the detectable substance in use, the first detector for producing a signal in response to detecting the substance in the flow of fluid;
    a second detector disposed downstream from the first detector in the path of the flow of fluid containing the detectable substance in use, the second detector for producing a signal in response to detecting the substance in the flow of fluid;
    a data system configured to receive the signals produced by the first and second detectors upon detecting the substance in the flow of fluid, the data system configured to compute a volumetric flow rate of the flow of fluid based on a time interval between the signals and a volume of the path between the first and second detectors; and
    a switch apparatus diverting the flow of fluid away from fraction collection towards at least one of the first and second detectors.

2. The flow rate measurement apparatus of claim 1, wherein the inserted substance is a gas bubble, and each of the first and second detectors is a bubble detector.

3. The flow rate measurement apparatus of claim 1, wherein the path leads to waste downstream of the second detector.

4. The flow rate measurement apparatus of claim 1, wherein the substance is inserted into the flow of fluid in response to the switch apparatus diverting the flow of fluid away from fraction collection.

5. The flow rate measurement apparatus of claim 1, wherein the switch apparatus is disposed downstream of the first detector to divert the flow of fluid away from fraction collection towards the second detector.

6. The flow rate measurement apparatus of claim 1, wherein the switch apparatus is disposed upstream of the first detector to divert the flow of fluid away from fraction collection towards the first and second detectors.

7. The flow rate measurement apparatus of claim 1, wherein the switch apparatus comprises a fraction collector including:
    a valve assembly having a plurality of ports;
    a dispensing needle in fluidic communication with a first port of the plurality of ports of the valve assembly;
    a syringe in fluidic communication with a second port of the plurality of ports of the valve assembly; and
    a controller in communication with the valve assembly and syringe to draw a gas bubble through the dispensing needle into the syringe, to flush the syringe in order to push the gas bubble into a waste line in fluidic communication with a third port of the plurality of ports of the valve assembly, and to switch the gas bubble into the path of the flow of fluid.

8. The flow rate measurement apparatus of claim 1, wherein the first detector comprises a sample-analysis detector.

9. The flow rate measurement apparatus of claim 1, further comprising a sample-analysis detector disposed in the path of flowing fluid upstream of the first detector.

10. A method for measuring a flow rate of a fluid passing through a chromatography system, the method comprising:
inserting a detectable substance into a flow of fluid;
producing a signal, by a first bubble detector disposed in a path of the flow of fluid containing the detectable substance, in response to detecting the substance in the flow of fluid;
producing a signal, by a second bubble detector disposed downstream from the first detector in the path of the flow of fluid with the detectable substance, in response to detecting the substance in the flow of fluid;
computing a volumetric flow rate of the flow of fluid based on a time interval between the signals and a volume of the path between the first and second detectors; and
switching the flow of fluid away from fraction collection to divert the flow of fluid towards at least one of the first and second detectors.

11. The method of claim 10, wherein the inserted substance is a gas bubble, and each of the first and second detectors is a bubble detector.

12. The method of claim 10, wherein the path leads to waste downstream of the second detector.

13. The method of claim 10, wherein inserting the detectable substance into the flow of fluid occurs in response to switching the flow of fluid away from fraction collection to divert the flow of fluid towards at least one of the first and second detectors.

14. The method of claim 10, wherein switching the flow of fluid away from fraction collection to divert the flow of fluid towards at least one of the first and second detectors occurs downstream of the first detector.

15. The method of claim 10, wherein switching the flow of fluid away from fraction collection to divert the flow of fluid towards at least one of the first and second detectors occurs upstream of the first detector.

16. The method of claim 10, wherein inserting the detectable substance into the flow of fluid comprises:
drawing a gas bubble through a dispensing needle into a syringe;
flushing the syringe to push the gas bubble into a waste line; and
switching a valve to place the gas bubble into the path of the flow of fluid.

* * * * *